US011602107B2

(12) United States Patent
Reeves et al.

(10) Patent No.: US 11,602,107 B2
(45) Date of Patent: *Mar. 14, 2023

(54) GRAFT-MEDIATED HYBRIDISATION OF MONOCOTYLEDONOUS PLANTS

(71) Applicant: CAMBRIDGE ENTERPRISE LIMITED, Cambridge (GB)

(72) Inventors: Gregory Reeves, Cambridge (GB); Julian Hibberd, Cambridge (GB)

(73) Assignee: CAMBRIDGE ENTERPRISE LIMITED, Cambridge (GB)

(*) Notice: Subject to any disclaimer, the term of this patent is extended or adjusted under 35 U.S.C. 154(b) by 0 days.

This patent is subject to a terminal disclaimer.

(21) Appl. No.: 17/293,765

(22) PCT Filed: Nov. 14, 2019

(86) PCT No.: PCT/GB2019/053231
§ 371 (c)(1),
(2) Date: May 13, 2021

(87) PCT Pub. No.: WO2020/099878
PCT Pub. Date: May 22, 2020

(65) Prior Publication Data
US 2022/0015311 A1  Jan. 20, 2022

(30) Foreign Application Priority Data
Nov. 14, 2018 (GB) ...................................... 1818577

(51) Int. Cl.
*A01H 6/46* (2018.01)
*A01H 1/06* (2006.01)
*A01H 1/02* (2006.01)

(52) U.S. Cl.
CPC .............. *A01H 1/02* (2013.01); *A01H 1/021* (2021.01); *A01H 1/06* (2013.01); *A01H 6/4624* (2018.05); *A01H 6/4636* (2018.05); *A01H 6/4654* (2018.05); *A01H 6/4666* (2018.05); *A01H 6/4678* (2018.05); *A01H 6/4684* (2018.05)

(58) Field of Classification Search
CPC . A01H 1/02; A01H 1/04; A01H 1/021; A01G 2/30
See application file for complete search history.

(56) References Cited

U.S. PATENT DOCUMENTS

| | | | |
|---|---|---|---|
| 2015/0114519 A1 | 4/2015 | Hyde et al. | |
| 2015/0272013 A1 | 10/2015 | Harada | |

FOREIGN PATENT DOCUMENTS

| | | | |
|---|---|---|---|
| CN | 105706897 A | 6/2016 | |
| CN | 105981594 A | * 10/2016 | ............... A01G 1/06 |

OTHER PUBLICATIONS

Stegemann, Sandra, and Ralph Bock. "Exchange of genetic material between cells in plant tissue grafts." science 324.5927 (2009): 649-651. (Year: 2009).*
Rouphael, Y., Venema, J.H., Edelstein, M., Savvas, D., Colla, G., Ntatsi, G., Ben-Hur, M., Kumar, P. and Schwarz, D. 2017. Grafting as a tool for tolerance of abiotic stress. In. Vegetable Grafting: Principles and Practices. Eds. Colla, et al. CAB International (U.K.), pp. 171-215. (Year: 2017).*
Laurie, D. A. "The frequency of fertilization in wheat* pearl millet crosses." Genome 32.6 (1989): 1063-1067. Supplemented by Applicant in IDS filed Nov. 30, 2021 (Year: 1989).*
Andrews et al., (1993). "Graft incompatibility," Hort. Rev., 15:183-232.
Baulcombe, (2005). "RNA silencing," Trends Biochem Sci., 30(6):290-293.
Bock, (2010). "The give-and-take of DNA: horizontal gene transfer in plants," Trends in Plant Science, 15(1):11-22.
Brosnan et al., (2007). "Nuclear gene silencing directs reception of long-distance mRNA silencing in *Arabidopsis*," PNAS USA, 104(37):14741-14746.
Calarco et al., (2012). "Reprogramming of DNA Methylation in Pollen Guides Epigenetic Inheritance via Small RNA," Cell, 151:194-205.
Calderini, (1846). "Essai d'experiences sur la graffe des graminées," Ann. Sci.Nat. Bot., 6:131-133, 4 pages. English translation.
Chung et al., (2007). "Rootstocks for grafting," Horticulture in Korea. Korean Society for Horticultural Science, 162-167.
Dransfield et al., (2008). "Genera Palmarum: the evolution and classification of palms," Royal Botanic Gardens, Kew, 745 pages.
Fuentes et al., (2014). "Horizontal genome transfer as an asexual path to the formation of new species," Nature, 511:232-235, 15 pages.
Goldschmidt, (2014). "Plant grafting: new mechanisms, evolutionary implications," Frontiers in Plant Sci., 5:727, 9 pages.
Harada, (2010). "Grafting and RNA transport via phloem tissue in horticultural plants," Scientia Horticulturae, 125:545-550.
Kanehira et al., (2005). "Apple phloem cells contain some mRNAs transported over long distances," Tree Genetics and Genomes, 6:635-642.
Katayama et al., (1996). "Phylogenetic affinities of the grasses to other monocots as revealed by molecular analysis of chloroplast DNA," Current Genetics, 29:572-581.
King et al., (2008). "Grafting for Disease Resistance," HortScience, 43(6):1673-1676.
Kumar, (2011). "Propagation of plants by grafting and budding," Revised Edition. Washington: Horticultural and Landscape Architecture, Washington State University, 18 pages.
Laurie, (1989). "The frequency of fertilization in wheat x pearl millet crosses," Genome, 32:1063-1067.
Lee et al., (2010). "Current status of vegetable grafting: Diffusion, grafting techniques, automation," Scientia Horticulturae, 127:93-105.
Lee, (1994). "Cultivation of Grafted Vegetables I. Current Status, Grafting Methods, and Benefits," HortScience, 29(4):235-239.
Liu et al., (2006). "Screening for High-Temperature Tolerant Cotton Cultivars by Testing In Vitro Pollen Germination, Pollen Tube Growth and Boll Retention," Journal of Integrative Plant Biology, 48(6):706-714.

(Continued)

*Primary Examiner* — Weihua Fan
(74) *Attorney, Agent, or Firm* — Morrison & Foerster LLP

(57) ABSTRACT

The invention relates to the production of graft-mediated hybrid monocotyledonous plants. Methods for the production of such plants are disclosed herein.

24 Claims, 8 Drawing Sheets

(56) References Cited

OTHER PUBLICATIONS

Louws et al., (2010). "Grafting fruiting vegetables to manage soilborne pathogens, foliar pathogens, arthropods and weeds," Scientia Horticulturae, 127:127-146.
Melnyk et al., (2015). "Plant grafting," Current Biology, 25(5):R183-R188.
Melnyk, (2017). "Plant grafting: insights into tissue regeneration," Regeneration, 4:3-14.
Molnar et al., (2010). "Small Silencing RNAs in Plants Are Mobile and Direct Epigenetic Modification in Recipient Cells," Science, 328:872-875.
Mudge et al., (2009). "A history of grafting," Horticultural reviews, 35:437-493.
Muzik et al., (1952). "The Grafting of Large Monocotyledonous Plants," Science, 116:589-591.
Muzik et al., (1954). "Further studies on the grafting of monocotyledonous plants," American Journal of Botany, 41:448-455.
Obolensky, (1960). "Grafting of plant embryos and the use of ultrasonics," Qualitas plantarum et materiae vegetabiles, 7:273-288, 32 pages.
Sachs, (1949). "Vegetative Hybridization," Nature, 164:1009-1010.
Sachs, (1951). "'Vegetative hybridization' in the tomato," Nature, 167:282-283.
Schwarz et al., (2010). "Grafting as a tool to improve tolerance of vegetables to abiotic stresses: Thermal stress, water stress and organic pollutants," Scientia Horticulturae, 127:162-171.
Stegemann et al., (2009). "Exchange of Genetic Material Between Cells in Plant Tissue Grafts," Science, 324:649-651.
Stubbe, (1954). "Über die vegetative Hybridisierung von Pflanzen," Die Kulturpflanze, 2:185-236, 56 pages. English Abstract.
TopoLeski et al., (1963). "A study of graft-induced alterations in eggplant," Proc. Am. Soc. Hortic. Sci., 83:559-570, 7 pages.
Tournier et al., (2006). "Phloem flow strongly influences the systemic spread of silencing in GFP Nicotiana benthamiana plants," Plant Journal, 47:383-394.
Trias-Blasi et al., (2015). "A genus-level phylogenetic linear sequence of monocots," Taxon, 64(3):552-581.
Turnbull, (2010). "Grafting as a research tool," Plant Developmental Biology, 655:11-26.
Van Nocker et al., (2014). "Breeding better cultivars, faster: applications of new technologies for the rapid deployment of superior horticultural tree crops," Horticulture Research, 1:22, 8 pages.
Wang et al., (2017). "Plant grafting: how genetic exchange promotes vascular reconnection," New Phytologist, 214:56-65.
Wu et al., (2013). "Inter-Species Grafting Caused Extensive and Heritable Alterations of DNA Methylation in Solanaceae Plants," PLoS ONE, 8(4):e61995, 11 pages.
Xu et al., (2013). "siRNA-mediated DNA methylation and H3K9 dimethylation in plants," Protein & Cell, 4(9):656-663.
Zeevaart, (2008). "Leaf-produced floral signals," Current opinion in plant biology, 11:541-547.

* cited by examiner

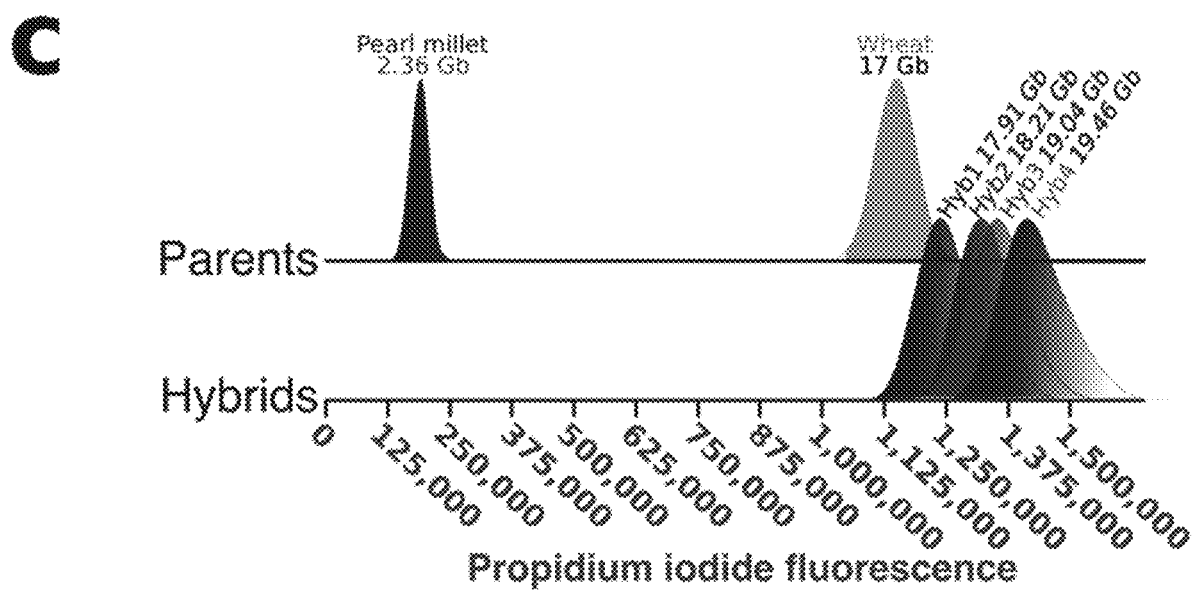
Figure 5 *(cont.)*

GRAFT-MEDIATED HYBRIDISATION OF MONOCOTYLEDONOUS PLANTS

CROSS REFERENCE TO RELATED APPLICATIONS

This application is a national stage application under 35 U.S.C. § 371 of International Application No. PCT/GB2019/053231, filed internationally on Nov. 14, 2019, which claims the priority benefit of Great Britain Application No. 1818577.7, filed on Nov. 14, 2018, each of which are hereby incorporated by reference in their entireties.

FIELD OF THE INVENTION

The invention relates to the production of graft-mediated hybrid monocotyledonous plants.

BACKGROUND OF THE INVENTION

Grafting is the horticultural practice of fusing two plants so that they grow as one. Nearly all perennial orchard crops and ornamentals (i.e. apple, cherry, pecan, grape, rose, olive, citrus, maple, etc.) as well as many high-value annual crop species are grafted commercially (Hartmann et al., 2010).

It is believed that the first use of plant grafting was for clonal propagation of desirable plant varieties (Mudge et al., 2009). For example, many orchard species are highly heterozygous, which means the traits of the parents will segregate in subsequent generations. Therefore, growth from seeds is not a viable way to maintain desirable genotypes. Moreover, certain tree species, such as apple (*Malus* sp.), are difficult to propagate by rooting cuttings. Instead, branches of a superior tree can be grafted to stocks of alternative accessions to produce clones.

Grafting can serve to improve certain characteristics, including disease resistance and the ability to adapt to extreme temperatures or to edaphic factors, such as salt tolerance (Lee, 1994; Louws et al., 2010; Schwarz et al., 2010). In many cases, a disease resistant rootstock is able to confer protection against soil borne pathogens when grafted to a susceptible scion (King et al., 2008). Thus, grafting can help increase the overall yield of the plant. For example, grafted melons yield 25-55% more than non-grafts (Lee et al., 2010), and a 51-54% increase in yield was observed when rootstocks 'Helper' and 'Kagemusia' were used in tomato grafts (Chung and Lee, 2007).

Grafting also enables one plant to be supported by multiple root systems or one root system to support multiple plants as branches. This can speed the growth of an individual scion or allow the propagation of multiple scions to conserve space. This is particularly useful in orchard crop breeding. Lastly, by grafting a juvenile $F_1$ hybrid seedling onto a mature rootstock, the hybrid may reach flowering many years sooner than if it had grown without grafting (Nocker and Gardiner, 2014).

Almost all reports of grafting specifically refer to dicotyledonous plant species, and in some cases gymnosperms or magnoliids. Successful grafting of monocotyledons is thought to be precluded because they lack vascular cambium tissue in their stems. Indeed, current consensus in the literature is that it is not possible to graft monocotyledons (Melnyk, 2017b; J. Wang et al., 2017; Melnyk and Meyerowitz, 2015; Kumar, 2011; Hyde et al., 2015; Turnbull, 2010; Zeevaart, 2008; Andrews and Marquez, 1993). Moreover, compared with the numerous reports of dicotyledonous grafting that span millennia, there are very few articles that claim monocotyledon grafting (Obolensky, 1960; Muzik and La Rue, 1952; Muzik and La Rue, 1954; Calderini, 1846), and these reports either lack a disclosure of the underlying methods, or their findings are of questionable validity because of their inconsistency with the current understanding of trait inheritance.

In any case, despite the occasional reports of grafting monocots, nobody has ever grafted banana (family Musaceae) or palm (family Arecaceae), nor have they formed hybrids in monocotyledons from regenerating graft junctions. Muzik and La Rue (1952, 1954), while having convincing evidence for successful graft unions between monocotyledons, grafted at internodes, stem junctions between leaf offshoots, of the plants. Internodes form in monocotyledons later into adulthood, and thus internode grafting precludes grafting in the seedling stage. This complicates the procedure and reduces the benefits of the scion/rootstock combination in the adult plant. Their success rates were also very low, on average 3%.

Calderini (1846) claimed to have grafted rice to *Echinochloa Crus-galli*, yet makes no mention of success rates nor the number of plants grown. Calderini (1846) stated that, by his means of grafting, he had produced a new strain of rice with superior characteristics, which is transmitted to the following generation. Obolensky (1960) reported placing the endosperm of winter wheat and the embryo of spring wheat in close contact. The plants derived by this endosperm/embryo exchange cannot be considered true grafts as this process does not lead to the fusion of tissues. In this case, he reported that 'deep hereditary changes were observed' in their offspring, such as conversion of a spring wheat variety into winter wheat variety via 'vegetative hybridization', a popularized concept in the Soviet Union at the time. Moreover, Obolensky (1960) also reported placing part of the endosperm from maize next to part of the endosperm from wheat and on the same seed replaced a section of the wheat mesocotyl with that of maize. Such plants produced consisted of rootstock and scion derived from a single wheat embryo but connected by the mesocotyl of maize.

Neither Calderini (1846) nor Obolensky (1960) provided evidence that their experiments yielded true grafts or showed that the plants had undergone any gene transfer to lead to heritable changes in the grafts. Thus, it is doubtful that the grafts produced by Obolensky (1960) or Calderini (1846) led to real hybrids. Instead, their phenotypic observations may likely have been explained by epigenetic effects, as has been reported in other studies (Calarco et al., 2012; Xu et al., 2013; Wu et al., 2013; Molnar et al., 2010; Brosnan et al., 2007; Baulcombe, 2005; Tournier et al., 2006; Z. Liu et al., 2006; Harada, 2010; Kanehira et al., 2005). The consensus among the scientific community, instead, is that, seemingly because of the structure of their vascular bundles, monocots cannot be grafted (Melnyk, 2017b; Wang et al., 2017; Melnyk and Meyerowitz, 2015; Kumar, 2011; Hyde et al., 2015; Turnbull, 2010; Zeevaart, 2008; Andrews and Marquez, 1993).

Without aid of selectable markers, which were not available at the time, these claims are doubtful. 'Vegetative hybridisation' or 'graft transformation', is highly controversial, and the phenotypes they report are not consistent with current understanding of genetics and inheritance. Many publications were not able to validate 'vegetative hybridization' nor presence of 'graft hybrids' (Sachs, 1949; Sachs, 1951; Stubbe, 1954; Topoleski and Janick, 1963). As there are poor routes to publish negative results, Goldschmidt (2014) claims there are likely many more unpublished studies which have likewise failed at 'vegetative hybridisation'.

Transfer of DNA between species at a graft junction has been reported in the *Nicotiana* genus in dicotyledons (Fuentes et al., 2014; Bock, 2010). However, as grafting was not considered possible in monocotyledons this has not been demonstrated outside of the dicotyledons, and it has not been demonstrated between species that do not belong to the same genus.

SUMMARY OF THE INVENTION

The present invention derives from the finding that, in fact, not only can monocots be grafted but also hybridisation can be achieved by grafting. Grafts between monocotyledonous plants can be made between or within species. These grafts can be performed in several monocotyledon families which are phylogenetically separated by many millions of years (Katayama and Ogihara, 1996; Soltis et al., 2018; Trias-Blasi et al., 2015), which implies that grafting within the monocotyledons is not restricted to specific families.

Disclosed herein is the regeneration of hybrid plants from monocotyledonous graft junctions. This approach has wide-ranging implications for commercial exploitation and provides a new mechanism to transfer DNA from one monocotyledonous species of crop to another. Indeed, examples such as *Triticale* or *Tritordeum* indicate that new monocotyledonous crops can be generated from sex-based wide-hybridisation events, and so regeneration from graft junctions also provides a new method to generate new types of crop.

A different tissue type is used herein to graft, and this results in much higher success rates. Herein provided is therefore a method of grafting the mesocotyl, i.e., grafting a plant at germination or as a young seedling. The benefits conferred by each tissue grafting partner are thus evident immediately. Additionally, much higher graft success rates are observed, on average 18-42%, depending on the species combination.

The invention provides a method of producing a hybrid monocot tissue or plant, comprising:
  (a) providing a first tissue comprising:
    (i) mesocotyl and radicle tissue; or
    (ii) mesocotyl and plumule tissue
    of a first monocot plant, wherein said first tissue comprises in its genome a first marker;
  (b) providing a second tissue comprising:
    (i) mesocotyl and radicle tissue; or
    (ii) mesocotyl and plumule tissue
    of a second, different monocot plant, wherein said second tissue comprises in its genome a second, different marker;
  (c) placing said first tissue in contact with said second tissue;
  (d) allowing fusion of the first and second tissues such that a graft junction forms, wherein said graft junction comprises at least one hybrid cell comprising said first and second markers;
  (e) selecting said at least one hybrid cell based on the presence of said first and second markers; and
regenerating a hybrid monocot tissue or plant from said at least one hybrid cell.

The invention further provides a grafted hybrid monocot tissue or plant, wherein said plant comprises genetic material from the first tissue and the second tissue, wherein said hybrid monocot tissue or plant is optionally obtained or obtainable by a method as defined above.

DETAILED DESCRIPTION OF THE INVENTION

Definitions

Figure 1:
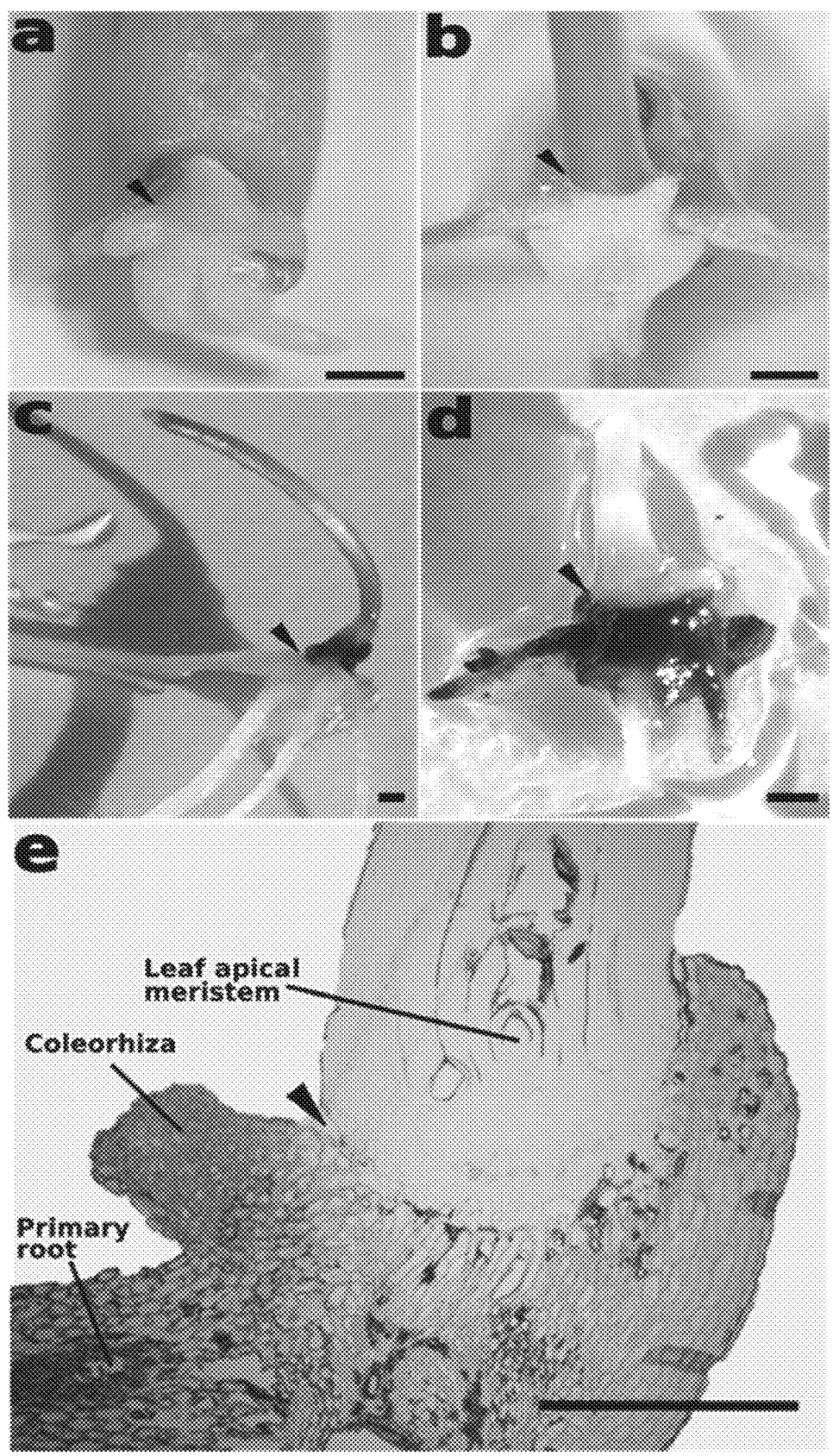
FIG. 1. Intraspecific wheat grafts fully reconnect vasculature and are stable throughout the lifecycle. a) Initial appearance of wheat (GUS$^-$) to wheat (GUS$^+$) embryo transplantation grafts, b) Graft fusion has already taken place after eight days, c) & d), distinction between rootstock and scion visualized by GUS staining after eight days, e) a thin section through the graft junction of an eight day old plant—the darker area under the graft junction is due to accumulation of the GUS reporter. The area above the graft does not stain and so is clear. f) A four month old intraspecific wheat graft. g), The graft union at harvest, h) & i), the graft junction is fully fused and seamless visualized by GUS staining. Arrowheads point to the graft junctions. Scale-bars represent 1 mm (a-e), 5 cm (f) and 5 mm (g-i).
Figure 1:
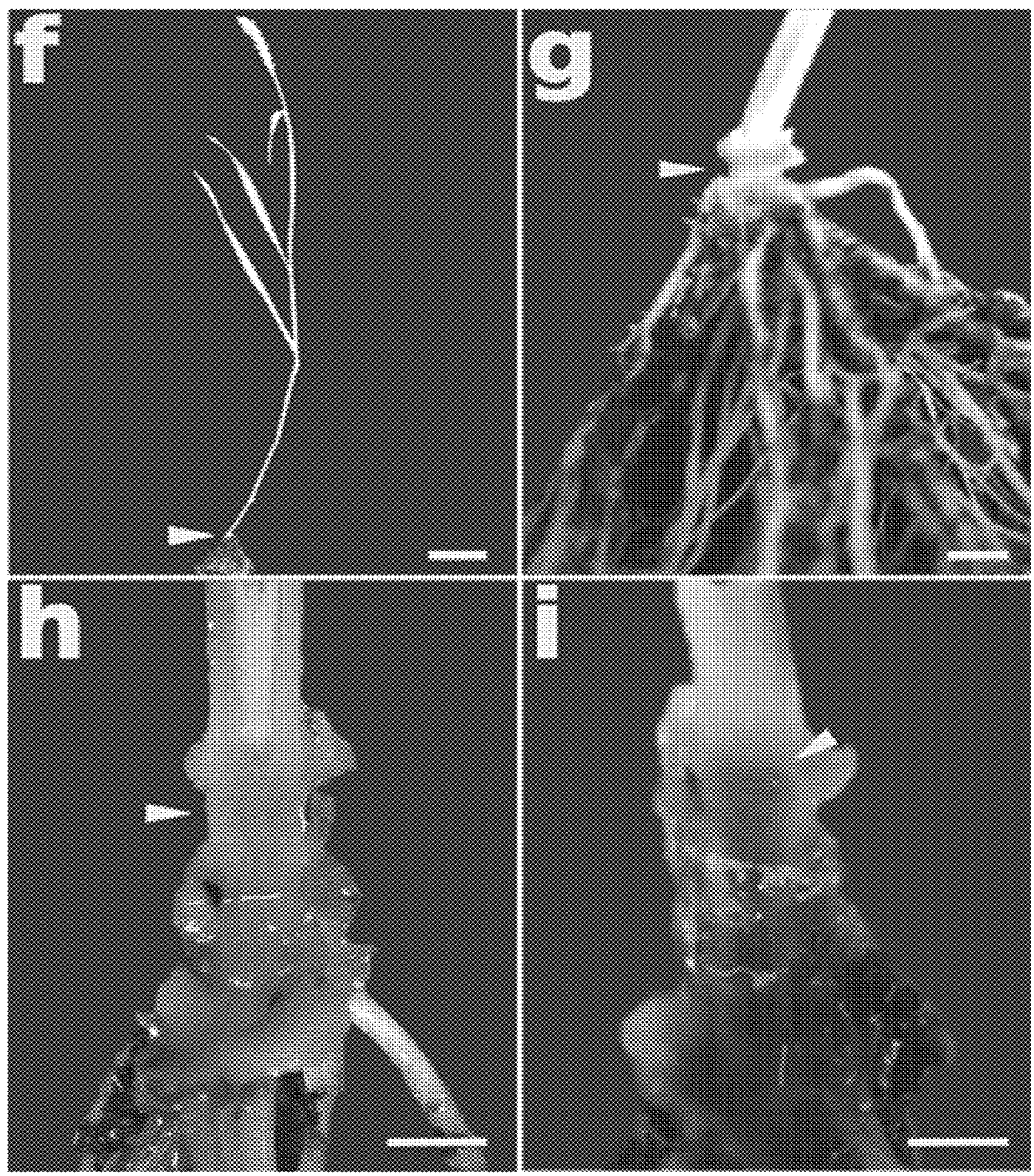
Figure 2:
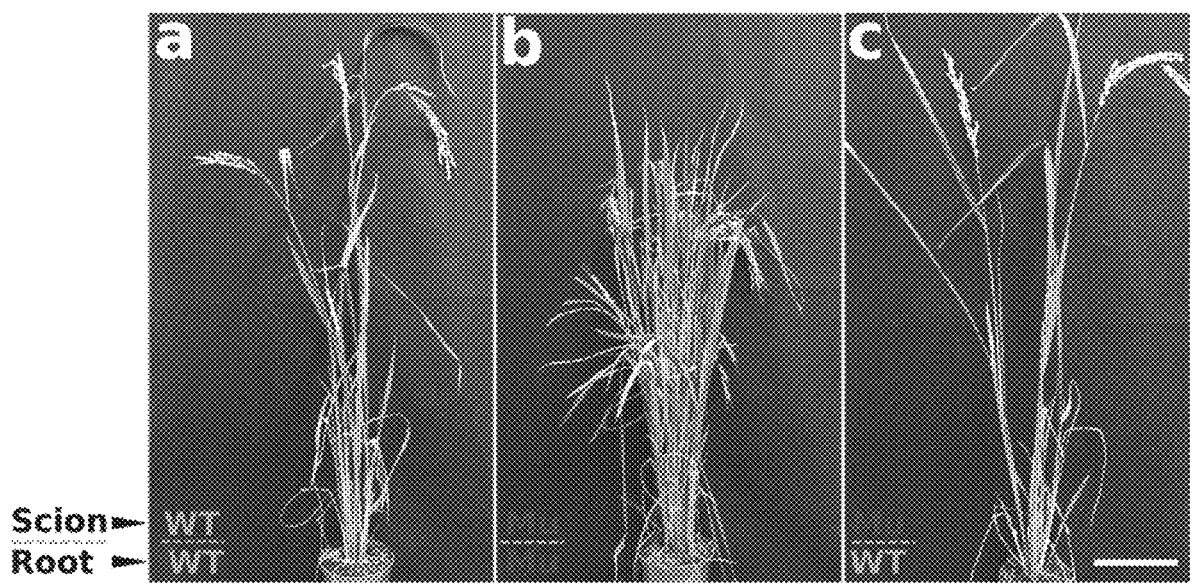
FIG. 2. Rice defective in strigolactone hormone biosynthesis is restored when grafted to a normal (wild type) rootstock. The appearance of a) wild type to wild type grafts, b) mutant to mutant grafts, and c) mutant to wild type grafts after 60 days of growth in soil. d) The number of tillers, e) the height of the tallest ligule, and f) the length of the longest leaf on each grafted plant measured over its lifespan. Error bars represent one standard error of the mean (n=4). Abbreviations: Wt, wild type (normal plants); Mu, mutant. Scale-bar represents 10 cm.
Figure 2:
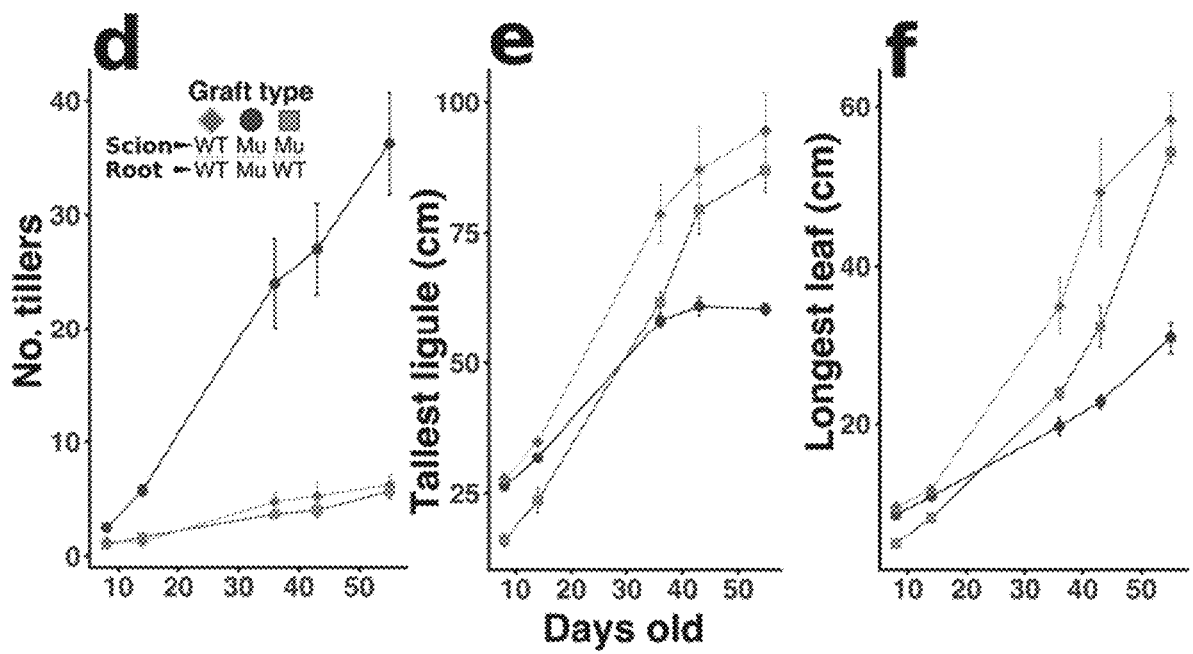
Figure 3:
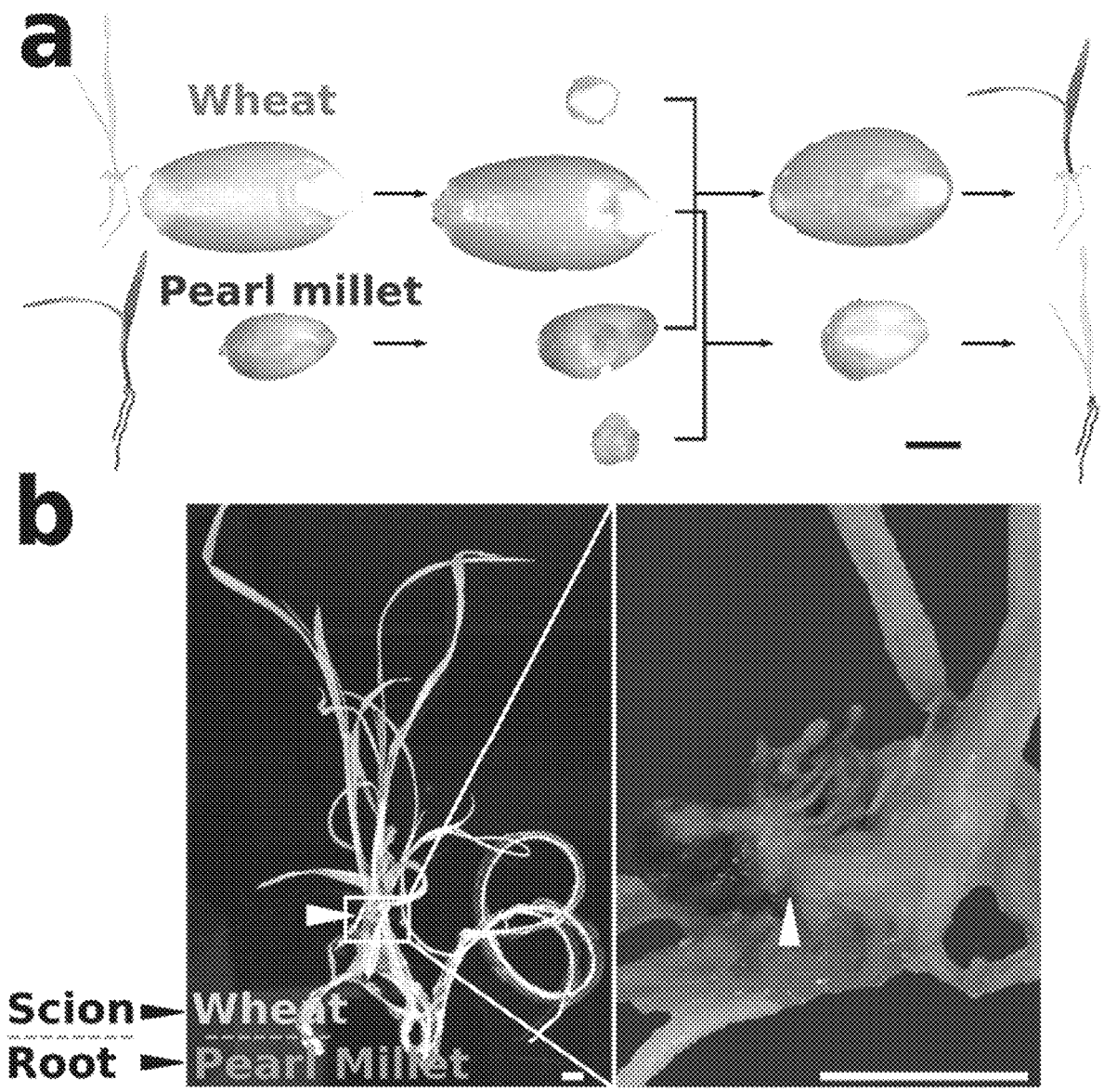
FIG. 3. Wheat and Pearl Millet Interspecific grafts. a) A schematic of embryonic grafting for wheat and pearl millet. b) A grafted plant after 5 weeks (left), a transverse section through the graft junction shows full reconnection between the rootstock and scion (right). Scale-bars represent 1.5 mm (a) and 5 mm (b).
Figure 4:
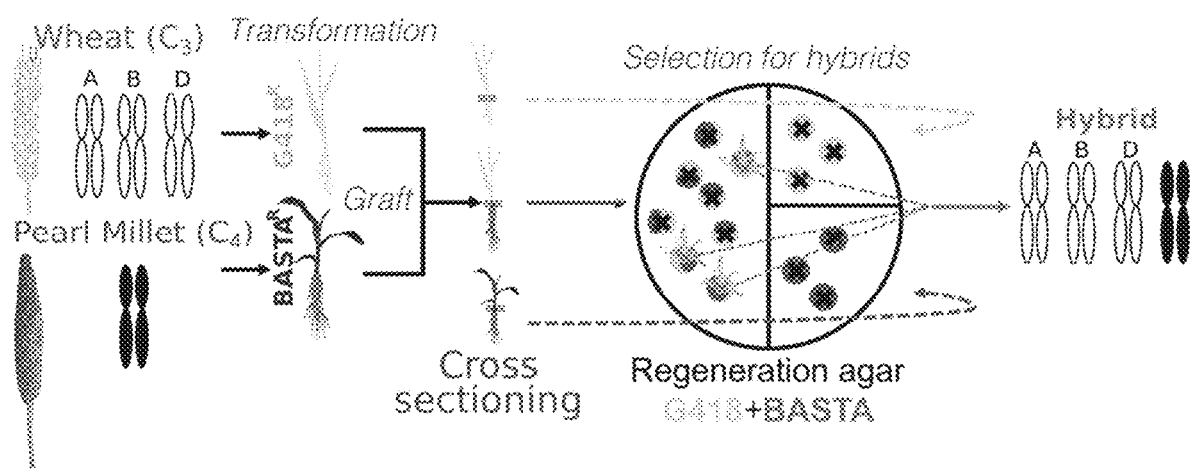
FIG. 4. An overview of hybridization of grafted monocots. Parental lines, here represented by wheat and pearl millet, are selected and transformed with different selectable marker genes. These are grafted together. Following fusion, the graft junction is sectioned and placed on regeneration media that contains selection agents that correspond to the selectable marker genes. This selects cells that contain genomes from both parents which grow into asexually produced hybrids.

Accession: A unique variety of a plant species.

Aneuploid: Possessing unequal or incomplete sets of chromosomes from either one species or multiple species.

Auxin: A class of plant hormone that regulate cell and plant growth.

Callus: Undifferentiated plant cells regenerating in tissue culture; proliferating tissue at the graft junction.

Cultivar: A plant accession that has been improved by selective breeding. It derives from merging cultivated and variety.

Dicotyledon, commonly referred to as a dicot: A flowering plant that typically contains two embryonic leaves in the seed, reticulate veins, and a taproot root system. Examples of dicots include many agronomic and horticultural plants, such as tomato, carrot, apple, oak, and soybean.

Endosperm: A tissue inside plant seeds that stores nutritious energy, in the form of starch, oil or protein, for the embryo.

Endogenous: Originating from within an organism.

Embryo: An immature plant, which has rudimentary tissue for the leaves, roots and stems. In flowering plants, the embryo is a part of the seed.

Epiblast: A flap-like projection connected to the coleorhiza, in the plant embryo.

Germination: The process by which a plant embryo begins to sprout and grow into a seedling.

Graft: The union of two plants so they grow as one (See Scion and Rootstock).

Graft, to: (v.) To place plant parts together to fuse them.

Graft junction: Tissue derived from two mesocotyl-comprising tissues that were united through grafting.

Hybrid: A first filial generation ($F_1$) plant derived from two genetically different parents.

Interspecific: between to different/separate species.

Intraspecific: within the same species.

Junction: The contact zone where the scion meets the rootstock in a grafted plant.

Marker: Any means of identifying the origin of a cell, tissue or plant. Markers comprise endogenous traits, selectable markers and visual markers.

Mesocotyl: The tissue between the shoot (plumule) and root (radicle). In most monocots, the mesocotyl can be easily found because it is directly below the epiblast, which is a flap-like projection on the exterior of the embryo.

Micropropagation: A tissue culture method for cloning plants on nutrient media, usually indefinitely.

Monocotyledon, commonly referred to as Monocot: A flowering plant that typically contains one embryonic leaf in the seed, parallel veins, and a fibrous root system. Examples of monocots include many agronomic crops and ornamental plants, such as all cereals (i.e., maize, wheat, rice), banana, palm, orchids, lilies, and tulips.

Monocotyledonous: (Adj.) of a monocotyledon.

Plumule: The embryonic shoot or leaves of a plant. In monocots, the plumule includes the coleoptile, embryonic leaves and shoot apical meristem.

Radicle: The embryonic root system of a plant. In monocots, the radicle is covered by the coleorhiza, a protective sheath.

Regeneration: A process of growing an adult plant from a single cell. Usually, this involves growing plants in tissue culture with hormones to proliferate and differentiate organs.

Rootstock: The root-bearing portion of a grafted plant.

Selectable marker: A nucleic acid sequence whose expression allows identification of cells, tissues or plants containing the nucleic acid sequence.

Selection agent: Any means of identifying cells, tissues or plants expressing a corresponding selectable marker. Selection agents include antibiotics, herbicides, toxins, salt and sugars.

Scion: The shoot-bearing portion of a grafted plant.

Tissue culture: A set of techniques that can be used to grow plants, plant cells, plant tissues, and organs in aseptic conditions on nutrient medium. Use of plant hormones can be used to regenerate adult plants from individual plant cells.

Plant Choice

To initiate the process, two plants are chosen for grafting. Any two plants that are closely related can be used. Grafting is preferably carried out between plants of the same genus, but can be performed between plants of the same family or order. Grafting can be carried out between plants of different species but of the same genus. Grafting can also be carried out between plants of different species but of the same family. Grafting can further be carried out between plants of different species but of the same order. Grafting can be carried out between plants of the same species but of a different genotype. Grafting can also be carried out between plants of the same species but of a different accession. Grafting can further be carried out between plants of the same species but of a different cultivar. Grafting can yet further be carried out between plants of the same species but of a different variety.

In some preferred pairings, either the tissue comprising mesocotyl and radicle tissue or the tissue comprising mesocotyl and plumule tissue is from a $C_3$ plant and the other one is from a $C_4$ plant. Preferably the trait of $C_4$ photosynthesis is conferred to the regenerated hybrid monocot tissue or plant derived from grafts of such tissues. $C_3$ plants include bread wheat (*Triticum aestivum*) and rice (*Oryza sativa*). $C_4$ plants include pearl millet (*Pennisetum glaucum*), sorghum (*Sorghum bicolor*) and maize (*Zea mays*).

In other preferred pairings, either the tissue comprising mesocotyl and radicle tissue or the tissue comprising mesocotyl and plumule tissue is from a salinity tolerant plant and the other is from a salinity intolerant plant. Preferably the trait of salinity tolerance is conferred to the regenerated hybrid monocot tissue or plant derived from grafts of such tissues. Salinity tolerant plants include *Oryza coarctata*, sea barley grass (*Hordeum marinum*) and tall wheatgrass (*Thinopyrum ponticum* or *Agropyron elongatum*). Salinity intolerant plants include rice (*Oryza sativa*), bread wheat (*Triticum aestivum*) and barley (*Hordeum vulgare*).

In other preferred pairings, either the tissue comprising mesocotyl and radicle tissue or the tissue comprising mesocotyl and plumule tissue is from a salinity tolerant $C_4$ plant and the other is from a salinity intolerant $C_3$ plant. Preferably the traits of $C_4$ photosynthesis and salinity tolerance are conferred to the regenerated hybrid monocot tissue or plant derived from grafts of such tissues. Salinity tolerant $C_4$ plants include *Sporobolus virginicus, Sporobolus stapfianus, Spartina* sp. Salinity intolerant $C_3$ plants include bread wheat (*Triticum aestivum*) and rice (*Oryza sativa*).

In other preferred pairings, either the tissue comprising mesocotyl and radicle tissue or the tissue comprising mesocotyl and plumule tissue is from a chilling tolerant plant and the other is from a chilling intolerant plant. Preferably the trait of chilling tolerance is conferred to the regenerated hybrid monocot tissue or plant derived from grafts of such tissues. Chilling tolerant plants include *Miscanthus×giganteus* and *Spartina* sp. Chilling intolerant plants include maize (*Zea mays*), sorghum (*Sorghum bicolor*) and pearl millet (*Pennisetum glaucum*).

In other preferred pairings, either the tissue comprising mesocotyl and radicle tissue or the tissue comprising mesocotyl and plumule tissue is from a freezing tolerant plant and the other is from a freezing intolerant plant. Preferably the trait of freezing tolerance is conferred to the regenerated hybrid monocot tissue or plant derived from grafts of such tissues. Freezing tolerant plants include winter rye (*Secale cereale*). Freezing tolerant plants include bread wheat (*Triticum aestivum*), barley (*Hordeum vulgare*) and rice (*Oryza sativa*).

In other preferred pairings, either the tissue comprising mesocotyl and radicle tissue or the tissue comprising mesocotyl and plumule tissue is from a drought tolerant plant and the other is from a drought intolerant plant. Preferably the trait of drought tolerance is conferred to the regenerated hybrid monocot tissue or plant derived from grafts of such tissues. Drought tolerant plants include *Zoysia* grass (*Zoysia japonica*), Bermuda grass (*Cynodon dactylon*), pearl millet (*Pennisetum glaucum*) and *Sporobolus* stapfianus. Drought intolerant plants include bread wheat (*Triticum aestivum*), rice (*Oryza sativa*) and barley (*Hordeum vulgare*).

In yet other preferred pairings, either the tissue comprising mesocotyl and radicle tissue or the tissue comprising mesocotyl and plumule tissue is from a pathogen resistant plant or pest resistant plant and the other is from a pathogen susceptible plant or pest susceptible plant. Preferably the trait of pathogen resistance or pest resistance is conferred to the regenerated hybrid monocot tissue or plant. For example, in such pairings, plants resistant to the pathogen *Puccinia graminis* (wheat stem rust) can be used, including rice (*Oryza sativa*), maize (*Zea mays*) or pearl millet (*Pennisetum glaucum*).

Seed Sterilisation

For the best results, grafting should be performed in aseptic conditions. Mature seeds of both plants are obtained and can be surface-sterilised. Any suitable sterilisation methodology may be used. In cereals, for example, seeds can be sterilised in 1-4% (v/v) sodium hypochlorite solution with 0.01% (v/v) Tween-20 or a similar surfactant for 20-45 minutes. The solution can be washed completely by several rinses of sterile water. Seeds can also, for example, be sterilised in 2-4% (v/v) Plant Preservative Mixture™ (PPM™, Apollo Scientific, UK) overnight or longer. PPM™ can be used to sterilise all monocotyledonous seeds and can be added in media (0.5% v/v) to greatly reduce contamination.

Partial Seed Germination

Germination of seeds can be initiated by any suitable method. In cereals, for example, the seeds can be soaked for 18-35 hours in sterile water between 20-30° C. in darkness. If PPM™ is used as the sterilisation agent, then the seeds may be kept in this solution during the germination phase. Soaking the seeds causes water absorption, which eases subsequent grafting steps. Soaking may be carried out for any suitable time period. Alternatively, dry seeds can be used. In perennial monocotyledons, for example banana and palm, seeds can for example be soaked for 3 days between 28-30° C. in darkness in a gibberellic acid ($GA_3$) solution, where the first day or longer in a mixture of 2-4% PPM™ (v/v) for sterilization and $GA_3$. In banana, 0.0002-0.001% (w/v) $GA_3$ is generally sufficient to initiate germination. In oil palm and date palm, 0.01-0.1% (w/v) $GA_3$ is generally sufficient to initiate germination.

Grafting of the Plant Embryo

Seeds of the two plants are taken. The seed coat can be present or be removed. If the seed coat is removed, it may be removed by any means, such as with a razor blade. The seeds can be dry or imbibed. Where the seeds are imbibed, they are preferably imbibed in water. Where the seeds are imbibed in water, they are preferably imbibed in water for 8 to 72 hours. The seeds can instead or additionally be partially germinated in the dark. Where the seeds are partially germinated in the dark, they preferably partially germinated in the dark for 2 to 30 days.

The two seeds are then cut. In some aspects, one seed will provide a tissue comprising mesocotyl and radicle tissue, while the other seed will provide a tissue comprising mesocotyl and plumule tissue. In other aspects, both seeds will provide a tissue comprising mesocotyl and radicle tissue. In yet other aspects, both seeds will provide a tissue comprising mesocotyl and plumule tissue.

In each seed, a transverse cut can be made across the mesocotyl, the differentiation point between the radicle and the plumule, inside the plant embryo. Greater success results from the thinnest blades, as the mesocotyl can be narrow. For example, a seed can be cut with a cutting edge with a thickness of 0.1 to 0.3 mm. The cut can be made with a blade, for example a razor blade. The cut can also be made with a tissue puncher. Preferably, a tissue puncher used for this purpose is 1.2 mm in diameter.

In some aspects, a first tissue comprising mesocotyl and plumule tissue can be excised from both seeds and exchanged between seeds and can be pressed in close contact with a second, different tissue comprising mesocotyl and radicle tissue. Optionally, an adhesive, grafting wax or a paste comprising soaked endosperm of the same grafting partner, can be applied to the edges of the graft junction to keep the two tissues in adhesion. Care must be taken to prevent the glue or other adhesive from seeping into the junction between the two tissues.

Alternatively, a hole puncher, preferably with a diameter of 1-1.25 mm, fitted with a plunger can instead be used to exchange embryonic pieces from dry or imbibed seeds. The bottom of the sharpened edge of the puncher can be placed mid-way over the epiblast of the seed comprising the first tissue comprising mesocotyl and radicle tissue. Gentle movement downward can then cut a hole into the seed to the endosperm which bisects the mesocotyl. The shoot can then be excised, and ejected by the plunger. Subsequently, tissue of another seed can be removed in the same manner, yet can be ejected into the hole bored into the first seed to align the two halves of the mesocotyl such that they are in direct contact with each other. An exact fit of embryo pieces is usually accomplished by this method as the diameter of the cut piece is determined by the diameter of the puncher. Aided by a puncher, a skilled technician can graft 60-100 plants per hour. When carefully grafted, embryo pieces demonstrate complete fusion between 18-42% of the time, depending on the combination.

Irrespective of the method used, the grafted seed is then typically kept in a moist/humid environment, usually on wet sterile filter paper, for 2-7 days until fusion occurs between the two tissues. Fusion means that functional vascular connections form between the two tissues. Preferably, the fusion step comprises growing the fused tissues on nitrocellulose membrane. For example, the grafted seed can be kept at a temperature of 20 to 28° C. in the dark for 2 to 4 days before exposure to light for 7 days. Any graft seedling can then optionally be transferred to soil under normal growing conditions.

Grafting Via Shoot Transplantation

Grafting can be performed on newly germinated seedlings. Germination can proceed until the plumule is 0.5-1 cm in length. The shoot is cut in the shape of a wedge or circle at the epiblast (see mesocotyl) and placed into a different seed which has had its plumula excised in the same manner. This approach is particularly useful for larger seeds, or when aiming to graft a shoot from a species that is sterile and so not able to make seeds onto an incipient root rootstock of a non-sterile recipient.

Grafting in Tissue Culture

Monocot grafting can be performed on plant tissue regenerated in tissue culture. Unlike most plants, cultivated banana is infertile, and as such, lacks the ability to form seeds. This makes it nearly impossible to obtain embryos from seeds. Instead, newly formed banana shoots can be micropropagated in tissue culture and then grafted to desirable rootstocks that have been micropropagated or isolated from embryos. Banana plants kept on nutrient media containing 6-Benzylaminopurine (BAP), an artificial cytokinin plant hormone, will continually proliferate shoots. If BAP is removed, then the shoots begin to form roots. Exploiting this, cultivated bananas can be grafted to desirable rootstocks. Banana shoots on BAP media are excised and are dissected to keep a single shoot connected to callus tissue from where they regenerate. These constitute the scion of the graft. Likewise, wild banana callus tissue (or embryonic roots from a germinated seed) serve as the rootstock. A callus of the same diameter which lacks a shoot is pressed in close contact to the wounded callus of the scion's callus. This is transferred to media without BAP. The period during which graft fusion is occurring between the calli also allows differentiation from the bottom callus to derive the root system.

Regeneration of Hybrids from the Graft Junction

The inventors found that monocots can exchange DNA from cell-to-cell at the graft junction. This combined with plant regeneration has been developed into a novel asexual hybridization method for monocots. Tissues of a first monocot plant and a second, different monocot plant can be grafted. In some aspects, a first tissue comprising mesocotyl and radicle tissue and a second tissue comprising mesocotyl and plumule tissue are grafted. In other aspects, a first tissue comprising mesocotyl and radicle tissue and a second tissue comprising mesocotyl and radicle tissue are grafted. In yet other aspects, a first tissue comprising mesocotyl and plumule tissue and a second tissue comprising mesocotyl and plumule tissue are grafted. The first and second tissues are placed in contact with each other and allowed to fuse so that a graft junction forms.

Any two tissues being grafted preferably comprise different markers. In some aspects, the first tissue and the second tissue comprise different selectable markers. In other aspects, the first tissue and the second tissue comprise different visual markers. In other aspects, the first tissue and the second tissue comprise different or complementary endogenous traits. In other aspects, one tissue comprises a selectable marker and the other tissue comprises a visual marker. In other aspects, one tissue comprises a selectable marker and the other tissue comprises an endogenous trait. In yet other aspects, one tissue comprises a visual marker and the other tissue comprises an endogenous trait. The two markers can then be used to select those cells from the graft junction which are hybrid cells, because these cells will comprise both markers.

The graft junction is derived from the two tissues and comprises at least one hybrid cell. Once fusion of the grafted tissues has occurred, the graft junction can be excised, preferably with a sterile blade. For example, sections spanning the graft site can be excised by cutting approximately 5 mm above and 5 mm below the graft junction. Sections can optionally be made through the graft junction to generate slices that preserve contact between the rootstock and scion. For example, thin longitudinal slices can be made through the graft junction to yield transverse sections that maintain the union between both the scion and rootstock.

Sections or sliced sections can then be placed in contact with tissue culture medium for regeneration. Typically, the sections or sliced sections remain on the medium for about one month to about one year. The regeneration medium (MEsocotyl Regeneration (MER) medium) to form hybrid tissue, such as multiple shoots or callus, can comprise a base medium (4.41 g·L$^{-1}$ Murashige and Skoog salts, 30 g·L$^{-1}$ maltose, 1 g·L$^{-1}$ N-Z amine, 500 mg·L$^{-1}$ proline, 200 mg·L$^{-1}$ myo-inositol, 1 mg·L$^{-1}$ thiamine HCl, 1.25 mg·L$^{-1}$ copper sulphate, and 3 g·L$^{-1}$ Gelrite™, at pH 5.8), and an auxin and a cytokinin as growth regulators. Numerous auxins and cytokinins are available for use as growth regulators. Either L 2,4-dichlorophenoxyacetic acid (2,4-D) or 4-amino-3,5,6 trichloropicolinic acid (picloram), as auxins, and thidiazuron (TDZ), as a cytokinin, offer good efficiency in regeneration of monocot mesocotyl graft junctions. Such a medium is, for example, able to regenerate wheat, barley, rice and pearl millet.

Preferably, the first and second markers are different selectable markers and the medium further comprises corresponding first and second selection agents to select tissue derived from hybrid cells comprising both markers. Where two different selectable markers are used, regenerating plants are typically sub-cultured every two weeks to fresh medium for 10 to 12 weeks on dual selection (medium containing both selection agents) to ensure that cells derived from either parent (which contain only one marker) do not grow. Instead, only cells that contain both markers (i.e., hybrid cells that have exchanged genomic DNA) are then able to grow. These cells can then regenerate into hybrid plants derived from the two plant species grafted together. For example, the antibiotic G418 and the herbicide glufosinate can be used as selection agents, but others are available, including antibiotics (such as kanamycin, hygromycin, paromomycin, etc), herbicides (such as glyphosate, imidazolinones, bialaphos, etc), toxins (such as 2-deoxyglucose, thialysine, methotrexate, cyanamide, sodium hypochloride, gabaculine, 4-methyl tryptophan and glycine betaine aldehyde) and other chemicals (such as salt, sugars, etc). The preferred working concentration for selection agents in regeneration medium range from 0.01 to 1000 mg·L$^{-1}$.

In order to initiate regeneration of graft junctions, 2 mg·L$^{-1}$ 2,4-D and 3 mg·L$^{-1}$ TDZ can be added to the base media to form MER initiation (MERi) media. Preferably, first and second different selectable markers are used and the medium further comprises corresponding first and second selection agents to select tissue derived from hybrid cells comprising both markers. For example, the antibiotic G418 and the herbicide glufosinate can be used as selection agents, but others are available, including antibiotics (such as kanamycin, hygromycin, paromomycin, etc), herbicides (such as glyphosate, imidazolinones, bialaphos, etc), toxins (such as 2-deoxyglucose, thialysine, methotrexate, cyanamide, sodium hypochloride, gabaculine, 4-methyl tryptophan and glycine betaine aldehyde) and other chemicals (such as salt, sugars, etc). The preferred working concentration for selection agents in regeneration medium range from 0.01 to 1000 mg·L$^{-1}$. In wheat and pearl millet, for example, the antibiotic G418 and the herbicide glufosinate can be used concentrations of 25 mg·L$^{-1}$ and 5 mg·L$^{-1}$ in the medium respectively.

To achieve regeneration into hybrid plants, hybrid tissue is placed on a shooting medium, preferably for one to two months, such that at least one hybrid shoot forms from said hybrid tissue. For example, the shooting medium (MER shooting (MERs) medium) can comprise MER base media with 0.1 mg·L$^{-1}$ 2,4-D and 1 mg·L$^{-1}$ TDZ. Then, the hybrid shoots or plantlets can be placed on rooting medium, preferably for two to four weeks, such that at least one hybrid monocot plant comprising roots forms. For example, the rooting medium (MER rooting (MERr) medium) can comprise MER base media with 0.5 mg·L$^{-1}$ IBA. Such hybrid plants can then be transferred to soil under normal growth conditions and used to breed or incorporate desirable traits from one species into the other via conventional methods.

Markers and Selection Agents

Any means of identifying the origin of a cell, tissue or plant can be used as a marker. Markers therefore comprise endogenous traits. In order to be useful as a marker, an endogenous trait should not be endogenous to both tissues being grafted. Endogenous traits include, for example, salinity tolerance, chilling tolerance, freezing tolerance, heavy metal detoxification, explosive detoxification and the ability to metabolise mannose, xylose or benzyladenine-N-3-glucuronide. Markers further comprise visual markers. Visual markers include fluorescent markers, GUS and luciferase.

Markers also comprise selectable markers. Any nucleic acid sequence whose expression allows identification of cells, tissues or plants containing the nucleic acid sequence can be used as a selectable marker. Selection agents useful to identify cells, tissues or plants expressing a corresponding selectable marker include antibiotics, herbicides, toxins, salt and sugars.

Antibiotics include, for example, kanamycin, geneticin (G418), hygromycin, paromomycin, neomycin, spectinomycin, streptomycin, gentamicin, tobramycin, apramycin, bleomycin, phleomycin, streptothricin and chloramphenicol.

Herbicides include, for example, glyphosate, glufosinate (or phosphinothricin/BASTA), bialaphos, chlorsulfuron, 3-(3,4-dichlorophenyl)-1,1-dimethylurea (DCMU), atrazine, paraquat, methyl viologen, metsulfuron-methyl, triclopyr, 3-Amino-1,2,4-triazole (3-AT), sulfonylureas, imidazolinones, triazolopyrimidines, pyrimidinyl oxybenzoates and sulfonylamino carbonyl triazolinones.

Toxins include, for example 2-deoxyglucose, thialysine, methotrexate, cyanamide, sodium hypochloride, gabaculine, 4-methyl tryptophan and glycine betaine aldehyde.

Sugars include, for example, mannose, xylose and benzyladenine-N-3-glucuronide. Where sugars are used as a selection agent, they are functional as limiting metabolites.

Traits of Interest

The methods of the present invention can then be used to incorporate desirable traits from one grafting partner tissue into the other. For example, the trait of $C_4$ photosynthesis can be conferred to a regenerated hybrid monocot tissue or plant derived from a graft between a tissue from a $C_3$ plant and a tissue from a $C_4$ plant. Other traits that can be conferred to the regenerated hybrid monocot tissue or plant include salinity tolerance, chilling tolerance, freezing tolerance, drought tolerance, perenniality, herbicide resistance, pathogen resistance, insect resistance, mite resistance, nematode resistance, parasitic plant resistance, herbivory resistance, nitrogen fixation, heat tolerance, wind tolerance, heavy metal tolerance, flooding and hypoxic stress tolerance, ozone tolerance, higher yield, lodging resistance, greater facilitation of mechanisation, anti-shattering of pods or seeds, altered plant height and stature, increased biomass, lower utilization of fertilizer, faster life-cycle, higher nutritional content, improved baking, milling and malting quality, improved taste, improved colour and longer shelf-life.

EXAMPLES

Example 1—Grafting Method

Seeds of each accession were surface sterilized. They can either be imbibed in water overnight (8-16 hours) or left dry. A tissue puncher with a 1.2 mm diameter and 0.1-0.3 mm thick cutting edge was used to bore out the entire plumule and half of the mesocotyl—the mesocotyl is bisected such that half of it is still connected with the plumule and the remaining half is still connected to the radicle of the imbibed seed. The incision was made directly through the seed coat (i.e., the seed coat is not removed beforehand). Alternatively, a 0.1-0.3 mm thick razor/scalpel blade can be used as an alternative tool to excise the plumule.

The removed plumule was replaced by one from a different seed (either from the same or different species), which can either be dry or imbibed. Dry plumule inserts appeared to absorb water from the imbibed seed causing them to swell, and this generated firm contact with the mesocotyl of the inserted plumule (scion source) and the radical in the seed (rootstock source) to form graft unions.

The grafts were allowed to germinate on nitrocellulose membranes placed on top of moist filter paper in petri plates with tall lids in darkness at 20-28° C. The membrane prevents roots from becoming embedded into the filter paper, and tall lids reduced the chance of graft junctions being pushed apart once the shoot elongated and pressed against the top of the container.

After incubation in darkness for two to four days, the seeds were exposed to light. A period of darkness following graft fusion encourages mesocotyl elongation and thus led to better fusion and a greater degree of success. Once graft fusion occurred, typically after 7 days, they were transferred to tissue culture conditions or optionally to soil.

Example 2—Graft-Mediated Hybridisation

After graft formation between species or accessions selected for hybridisation, sections spanning the graft site were excised by cutting approximately 5 mm above and 5 mm below the junction. Longitudinal slices were then made with a 0.1 mm thick scalpel through the junction to yield transverse sections that maintained the union between both the scion and rootstock.

The slices were placed on MERi media for one month. Regeneration of multiple shoots or callus formation from mesocotyl graft junctions was initiated on MEsocotyl Regeneration (MER) media consisting of a base media (4.41 g·L$^{-1}$ Murashige and Skoog salts, 30 g·L$^{-1}$ maltose, 1 g·L$^{-1}$ N-Z amine, 500 mg·L$^{-1}$ proline, 200 mg·L$^{-1}$ myo-inositol, 1 mg·L$^{-1}$ thiamine HCl, 1.25 mg·L$^{-1}$ copper sulphate, and 3 g·L$^{-1}$ Gelrite™, at pH 5.8), and an auxin (2,4-D) and a cytokinin (TDZ) as growth regulators. In order to initiate regeneration of graft junctions, 2 mg·L$^{-1}$ 2,4-D and 3 mg·L$^{-1}$ TDZ was added to the base media to form MER initiation (MERi) media. Media was dispensed in 9 cm diameter sterilin petri plates and sealed with parafilm. The MER media also contained suitable concentrations of selectable agents. For wheat and pearl millet, these were the antibiotic G418 and the herbicide glufosinate at 25 mg·L$^{-1}$ and 5 mg·L$^{-1}$, respectively. MER media is able to regenerate wheat, barley, rice and pearl millet. Multiple wheat varieties were tested for regeneration on MER with similar efficiencies. Thus, not only can MER regenerate accessions within a species in a genotype-independent manner, but also can regenerate different monocotyledonous species. Light intensity was maintained at 80 μmol photos m$^{-2}$s$^{-1}$ and photoperiod set to 16 hours of light and 8 hours of dark, with temperatures of 25.5° C. and 23.5° C. respectively.

Tissue was sub-cultured every two weeks onto fresh MER media for approximately 10-12 weeks on dual selection (media containing two selection agents, such as the antibiotic G418 and the herbicide glufosinate). Double selection ensures that cells derived from only one parent (which contain only one selectable marker) do not grow. Instead, only cells that contain both selectable markers (i.e., hybrid cells that have exchanged genomic DNA) were able to grow. Shoots appear from callus that is resistant to both selectable markers between 2 and 4 weeks. These cells regenerate into hybrid plants derived from both species grafted together.

In addition to G418 and glufosinate, a greater number of selectable agents are available, including antibiotics (such as kanamycin, hygromycin, paramomycin, etc), herbicides (such as glyphosate, imidazolinones, bialaphos, etc), toxins (such as 2-deoxyglucose, thialysine, methotrexate, cyanamide, sodium hypochloride, gabaculine, 4-methyl tryptophan and glycine betaine aldehyde) or other chemicals (such as salt, sugars, etc). The preferred working concentration for selection agents in regeneration media range between 0.01 to 1000 mg·L$^{-1}$.

Following this phase, regenerated shoots were placed on MER shooting (MERs) media which consisted of the MER base media with 0.1 mg·L$^{-1}$ 2,4-D and 1 mg·L$^{-1}$ TDZ for an additional one to two months. Once plantlets were formed on MERs media, they were rooted on MER rooting (MERr) media which consisted of MER base media with 0.5 mg·L$^{-1}$ IBA. Rooting usually occurs within two to four weeks. Once regenerated plants formed roots, these were transferred to soil under normal growth conditions. Hybrid plants were then available for use to breed or incorporate desirable traits from one species into the other via conventional methods.

Example 3—Grafting Wheat to Wheat (Intraspecific Grafting)

Transgenic wheat containing the β-glucuronidase (GUS) gene, which dyes plant tissue blue in the presence of X-gluc, was grafted to wild type wheat (non-transgenic) via embryo transplantation. After 2-4 days, fusion begins to occur resulting in an overall efficiency of around 32% (n=330). After 8 days, grafted plants were stained with X-gluc to reveal the graft junction. The contact layer (graft junction) of the plants appears as a dark line early in the graft fusion process but fades away during vascular reconnection. Grafted plants survive the entire lifecycle, even following flowering and seed set. A section through a GUS stained graft plant after four months shows that the contact layer has formed into complete vascular reconnection.

Example 4—Grafting Rice to Rice (Intraspecific Grafting)

Rice with defective hormone synthesis ability was grafted. Strigolactones are plant hormones that control tillering (branching), and impact on the ability to colonise beneficial fungi in their roots. As strigolactones can circulate throughout the plant, it was be expected that a mutant for strigolactone production to have normal branching restored if grafted successfully to a normal (wild type) rootstock. Mutant rice for the carotenoid cleavage dioxygenase 8 (CCD8) gene were grafted to wild type (non-mutant) rice rootstocks. As expected, the mutant to mutant grafts exhibited a large degree of branching, but the mutant to wild type grafts had the same branching habit as the wild type to wild type grafts. These plants maintained a normal appearance despite containing the mutation for the CCD8 gene. This indicates that not only is the graft union functional, and stable over time, but that the scion and rootstock are able to exchange endogenous substances including hormones.

Example 5—Grafting Wheat to Pearl Millet (Interspecific Grafting)

Wheat is a major global crop which accounts for approximately 20% of human food supply (rice accounts for a similar amount), yet uses an inefficient photosynthetic $CO_2$ fixation pathway, known as $C_3$ photosynthesis. If the more efficient $C_4$ photosynthetic pathway could be transferred into wheat, yields would be expected to increase by 50% with no need for additional land, water or fertilizer. Via embryonic grafting, it was found that wheat and pearl millet form functional graft reconnections with a success rate of approximately 25% (n=1423). Graft junctions were then regenerated to obtain hybrid plants.

Figure 5:
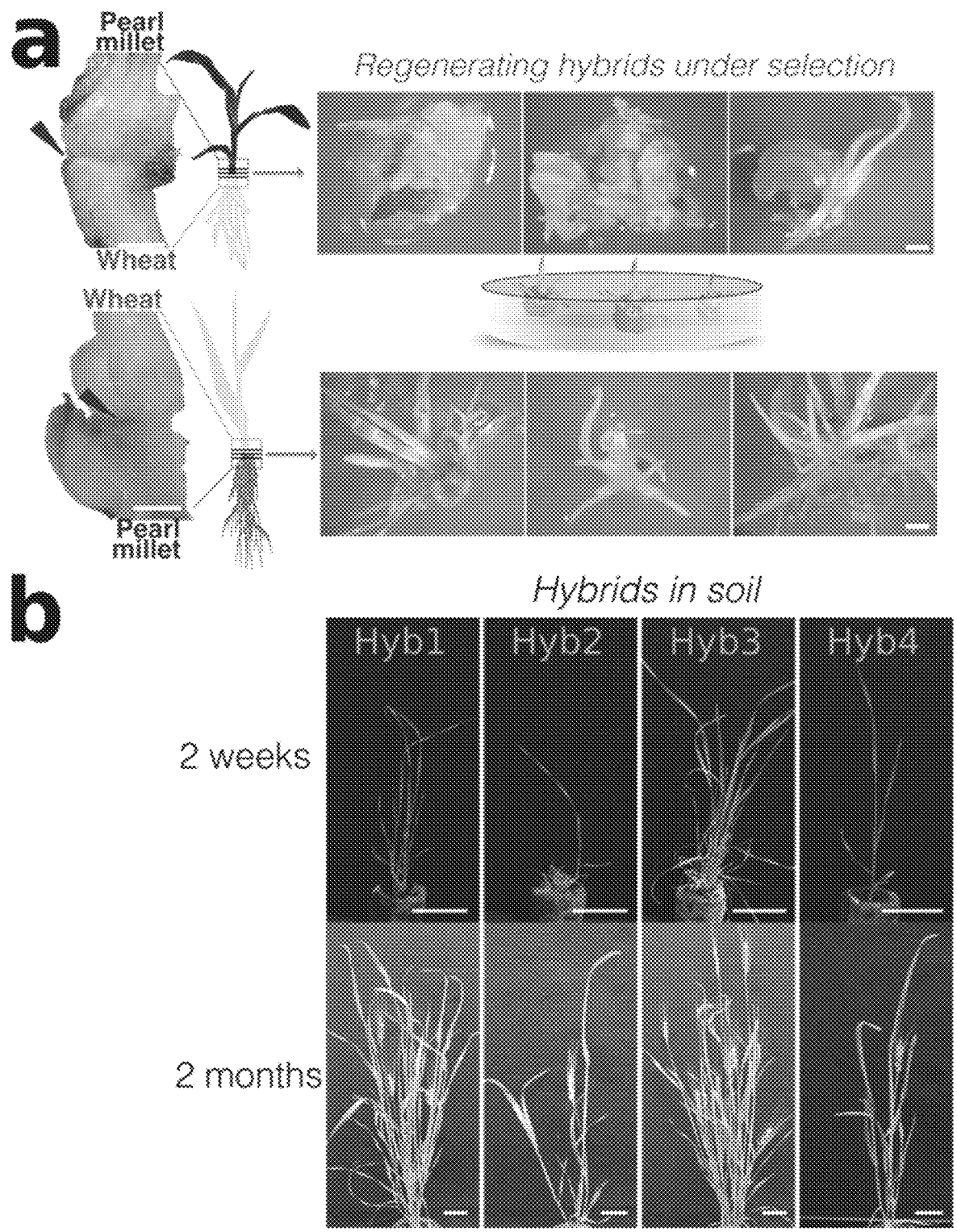
FIG. 5. Regeneration of wheat and pearl millet hybrids from graft junctions. a) The graft junction of wheat and pearl millet which are resistant to the selective herbicides G418 and BASTA, respectively, were regenerated into shoot and callus in tissue culture under selection pressure to produce hybrid tissue. Black arrowheads indicate the graft junction. b) Regenerated hybrid plants in soil after 2 weeks and 2 months of growth. c) The relative genome size comparison of several example hybrids to wheat and pearl millet as determined by flow cytometry. Scale-bars represent 1 mm (a) and 5 cm (b).

Wheat and pearl millet regenerate on MER media. Wheat that is resistant to the herbicide/antibiotic G418 was grafted to pearl millet that is resistant to the herbicide glufosinate (FIG. 5). The graft junctions between these two resistant accessions were regenerated on MER media that contained both G418 (17.5 mg·L$^{-1}$) and glufosinate (3.5 mg·L$^{-1}$). Callus formation occurred after several weeks and plants fully regenerated in 10-14 weeks. Genome size estimation by flow cytometry indicated that hybrids regenerated via this approach were intermediate to both wheat and pearl millet. This indicated that the plants regenerated had the presence of at least some of both species (aneuploid hybrids). These plants resemble pearl millet, but have characteristics of wheat. These plants are self-fertile whose seeds germinate normally. Some of these additionally had intermediate carbon isotope compositions, which is indicative of a photosynthetic mechanism intermediate to $C_3$ and $C_4$.

Plants that appeared to have the full complement of both genomes of wheat and pearl millet were recovered, suggesting that the grafting and hybridisation method can lead to the formation of breeding lines to introduce important traits for crop improvement. In general, these plants mostly resembled wheat, and their offspring maintained the genome of wheat and pearl millet into the subsequent generation. This indicated that DNA can be transferred across graft junctions and be incorporated stably into a sexually-incompatible species over multiple generations.

BIBLIOGRAPHY

Andrews, P. K. and C. S. Marquez (1993). Graft incompatibility. *Hort. Rev.* 15, 183-232

Baulcombe, D. (2005). RNA silencing. *Trends Biochem Sci* 30, 290-293

Bock R. (2010) The give-and-take of DNA: horizontal gene transfer in plants. *Trends in Plant Science* 1, 11-22

Brosnan, C. A., N. Mitter, M. Christie, N. A. Smith, P. M. Waterhouse and B. J. Carroll (2007). Nuclear gene silencing directs reception of long-distance mRNA silencing in *Arabidopsis. Proceedings of the National Academy of Sciences of the United States of America* 104, 14741-14746

Calarco, J. P., F. Borges, M. T. Donoghue, F. Van Ex, P. E. Jullien, T. Lopes, R. Gardner, F. Berger, J. A. Feijo, J. D. Becker and R. A. Martienssen (2012). Reprogramming of DNA Methylation in Pollen Guides Epigenetic Inheritance via Small RNA. *Cell* 151, 194-205

Calderini, I. M. (1846). Essai d'expériences sur la graffe des graminées. *Ann. Sci. Nat. Bot. III*, 131-133

Chung, H. D. and J.-M. Lee (2007). Rootstocks for grafting. *Horticulture in Korea. Korean Society for Horticultural Science*, 162-167

Dransfield, J., N. W. Uhl and Kew Royal Botanic Gardens (2008). Genera *Palmarum*: the evolution and classification of palms. Kew Pub. 732

Fuentes, I., S. Stegemann, H. Golczyk, D. Karcher and R. Bock (2014). Horizontal genome transfer as an asexual path to the formation of new species. *Nature* 511, 232-235

Goldschmidt, E. E. (2014). Plant grafting: new mechanisms, evolutionary implications. Frontiers in *Plant Sci.*, 5, 727

Harada, T. (2010). Grafting and RNA transport via phloem tissue in horticultural plants. *Scientia Horticulturae* 125, 545-550

Hartmann, H. T., D. E. Kester, F. T. J. Davies and R. L. Geneve (2010). Plant propagation: principles and practices. 8th. Prentice Hall/Pearson, 928

Hyde, R. A., M. Y. Ishikawa, R. C. Petroski, D. B. Tuckerman, T. A. Weaver, V. Y. H. Wood and L. L. Wood (2015). Harvesting and grafting of trees. U.S. patent application Ser. No. 14/069,079

Kanehira, A., K. Yamada, T. Iwaya, R. Tsuwamoto, A. Kasai, M. Nakazono and T. Harada (2005). Apple phloem cells contain some mRNAs transported over long distances. *Tree Genetics and Genomes* 6, 635-642

Katayama, H. and Y. Ogihara (1996). Phylogenetic affinities of the grasses to other monocots as revealed by molecular analysis of chloroplast DNA. *Current Genetics* 29, 572-581

King, S. R., A. R. Davis, W. Liu and A. Levi (2008). Grafting for Disease Resistance. *HortScience* 43, 1673-1676

Kumar, G. N. M. (2011). Propagation of plants by grafting and budding. Revised Edition. Washington: Horticultural and Landscape Architecture, Washington State University, 16

Lee, J.-M. (1994). Cultivation of Grafted Vegetables I. Current Status, Grafting Methods, and Benefits. *HortScience* 29, 235-239

Lee, J.-M., C. Kubota, S. J. Tsao, Z. Bie, P. Hoyos Echevarria, L. Morra and M. Oda G. A. Honorary (2010). Current status of vegetable grafting: Diffusion, grafting techniques, automation. *Scientia Horticulturae* 127, 93-105

Liu, Z., Y.-L. Yuan, S.-Q. Liu, X.-N. Yu and L.-Q. Rao (2006). Screening for High-Temperature Tolerant Cotton Cultivars by Testing In Vitro Pollen Germination, Pollen Tube Growth and Boll Retention. *Journal of Integrative Plant Biology* 48, 706-714

Louws, F. J., C. L. Rivard and C. Kubota (2010). Grafting fruiting vegetables to manage soilborne pathogens, foliar pathogens, arthropods and weeds. *Scientia Horticulturae* 127, 127-146

Melnyk, C. W. and E. M. Meyerowitz (2015). Plant grafting. *Current Biology* 25, R183-R188

Melnyk, C. W. (2017b). Plant grafting: insights into tissue regeneration. *Regeneration* 4, 3-14

Molnar, A., C. W. Melnyk, A. Bassett, T. J. Hardcastle, R. Dunn and D. C. Baulcombe (2010). Small Silencing RNAs in Plants Are Mobile and Direct Epigenetic Modification in Recipient Cells. *Science* 328, 872-875

Mudge, K., J. Janick, S. Scofield and E. E. Goldschmidt (2009). A history of grafting. *Horticultural reviews* 35, 437-493

Muzik, T. J. and C. D. La Rue (1952). The Grafting of Large Monocotyledonous Plants. *Science* 116, 589-591

Muzik, T. J. and C. D. La Rue (1954). Further studies on the grafting of monocotyledonous plants. *American Journal of Botany*, 448-455

Nocker, S. van and S. E. Gardiner (2014). Breeding better cultivars, faster: applications of new technologies for the rapid deployment of superior horticultural tree crops. *Horticulture Research* 1, 14022

Obolensky, G. (1960). Grafting of plant embryos and the use of ultrasonics. *Qualitas plantarum et materiae vegetabiles* 7, 273-288

Sachs, L. (1949). 'Vegetative Hybridization'. *Nature* 164, 1009

Sachs, L. (1951). 'Vegetative hybridization' in the tomato. *Nature* 167, 282

Schwarz, D., Y. Rouphael and J. H. Venema (2010). Grafting as a tool to improve tolerance of vegetables to abiotic stresses: Thermal stress, water stress and organic pollutants. *Scientia Horticulturae* 127, 162-171

Soltis, D. E., P. S. Soltis, P. K. Endress, M. W. Chase, S. R. Manchester, W. S. Judd, L. C. Majure and E. Mavrodiev (2018). Phylogeny and evolution of the angiosperms. *University of Chicago Press* 580

Stubbe, H. (1954). Über die vegetative Hybridisierung von Pflanzen. *Die Kulturpflanze* 2, 185-236

Topoleski, L. D. and J. Janick (1963). A study of graft-induced alterations in eggplant. *Proc. Am. Soc. Hortic. Sci.* 83, 559-570

Tournier, B., M. Tabler and K. Kalantidis (2006). Phloem flow strongly influences the systemic spread of silencing in GFP *Nicotiana benthamiana* plants. *Plant Journal* 47, 383-394

Trias-Blasi, A., W. J. Baker, A. L. Haigh, D. A. Simpson, O. Weber and P. Wilkin (2015). A genus-level phylogenetic linear sequence of monocots. *Taxon* 64, 552-581

Turnbull, C. G. N. (2010). Grafting as a research tool. *Plant Developmental Biology*. Springer, 11-26

Wang, J., L. Jiang and R. Wu (2017). Plant grafting: how genetic exchange promotes vascular reconnection. *New Phytologist* 214, 56-65

Wu, R., X. Wang, Y. Lin, Y. Ma, G. Liu, X. Yu, S. Zhong and B. Liu (2013). Inter-Species Grafting Caused Extensive and Heritable Alterations of DNA Methylation in Solanaceae Plants. *PLoS ONE* 8, e61995

Xu, C., J. Tian and B. Mo (2013). siRNA-mediated DNA methylation and H3K9 dimethylation in plants. *Protein & Cell* 4, 656-663

Zeevaart, J. A. D. (2008). Leaf-produced floral signals. *Current opinion in plant biology* 11, 541-547

The invention claimed is:

1. A method of producing a hybrid monocot tissue or plant, comprising:
   (a) providing a first tissue comprising:
      (i) mesocotyl and radicle tissue; or
      (ii) mesocotyl and plumule tissue
      of a first monocot plant, wherein said first tissue comprises in its genome a first marker;
   (b) providing a second tissue comprising:
      (i) mesocotyl and radicle tissue; or
      (ii) mesocotyl and plumule tissue
      of a second, different monocot plant, wherein said second tissue comprises in its genome a second, different marker;
   (c) placing said first tissue in contact with said second tissue;
   (d) allowing fusion of the first and second tissues such that a graft junction forms, wherein said graft junction comprises at least one hybrid cell comprising said first and second markers;
   (e) selecting said at least one hybrid cell based on the presence of said first and second markers; and (f) regenerating a hybrid monocot tissue or plant from said at least one hybrid cell.

2. The method of claim 1, wherein said first tissue comprises mesocotyl and plumule tissue and said second tissue comprises mesocotyl and radicle tissue.

3. The method of claim 1, wherein after step (d) and before step (e), said graft junction is cut to provide at least one longitudinal graft junction section, wherein said graft junction section comprises said at least one hybrid cell comprising said first and second markers.

4. The method of claim 1, wherein said first marker and/or said second marker is a selectable marker, wherein said selectable marker is selectable with a selection agent.

5. The method of claim 1, wherein said first marker and/or said second marker is a visual marker.

6. The method of claim 1, wherein said first marker and/or said second marker is an endogenous trait, wherein said endogenous trait is not endogenous to both the first tissue and the second tissue.

7. The method of claim 1, wherein said first marker and said second marker are selectable markers, wherein said first selectable marker is selectable with a first selection agent and said second selectable marker is selectable with a second, different selection agent.

8. The method of claim 4, wherein said first selection agent and/or said second selection agent comprises:
   (i) an antibiotic;
   (ii) a herbicide;
   (iii) a toxin;
   (iv) salt; or
   (v) a sugar.

9. The method of claim 8, wherein:
   (i) said antibiotic is selected from the group consisting of: kanamycin, geneticin (G418), hygromycin, paramomycin, neomycin, spectinomycin, streptomycin, gentamicin, tobramycin, apramycin, bleomycin, phleomycin, streptothricin, and chloramphenicol;
   (ii) said herbicide is selected from the group consisting of: glyphosate, glufosinate (or phosphinothricin/BASTA), bialaphos, chlorsulfuron, 3-(3,4-dichlorophenyl)-1,1-dimethylurea (DCMU), atrazine, paraquot, methyl viologen, metsulfuron-methyl, triclopyr, 3-Amino-12, 4-triazole (3-AT), a sulfonylurea, an imidazolinone, a triazolopyrimidine, a pyrimidinyl oxybenzoate, and a sulfonylamino carbonyl triazolinone;
   (iii) said toxin is selected from the group consisting of: 2-deoxyglucose, thialysine, methotrexate, cyanamide, sodium hypochloride, gabaculine, 4-methyl tryptophan, and glycine betaine aldehyde; or
   (iv) said sugar is selected from the group consisting of: mannose, xylose and benzyladenine-N-3-glucuronide.

10. The method of claim 7, wherein said regenerating comprises
   placing said graft junction or graft junction section on a base medium comprising at least one auxin, at least one cytokinin and said first and second selection agents such that hybrid tissue forms from said hybrid cell.

11. The method of claim 1, wherein the first tissue and/or the second tissue are provided:
   (i) from a first seed and a second seed; and/or
   (ii) by micropropagation in tissue culture.

12. The method of claim 11, wherein said first seed and/or said second seed comprises its seed coat.

13. The method of claim 11, wherein said first seed and/or said second seed:
   (i) is dry or imbibed in water; and/or
   (ii) is partially germinated in the dark.

14. The method of claim 11, wherein said first seed is imbibed in water and said second seed is dry.

15. The method of claim 11, wherein:
   (i) said first and/or said second seed is transversely cut and/or
   (ii) said first and/or said second seed is cut with a tissue puncher.

16. The method of claim 11, wherein the first tissue and/or the second tissue is tissue cultured on nutrient medium containing a cytokinin.

17. The method of claim 1, wherein the first tissue and the second tissue are from the same species.

18. The method of claim 1, wherein the first tissue and the second tissue are from different species within the same order.

19. The method of claim 18, wherein either one of the first tissue and the second tissue is from a $C_3$ plant and the other one is from a $C_4$ plant.

20. The method of claim 18, wherein either one of the first tissue and the second tissue is:
   (i) from a salinity tolerant plant and the other is from a salinity intolerant plant; or
   (ii) from a salinity tolerant $C_4$ plant and the other is from a salinity intolerant $C_3$ plant.

21. The method of claim 18, wherein either one of the first tissue and the second tissue is:
   (i) from a chilling tolerant plant and the other is from a chilling intolerant plant; or
   (ii) from a freezing tolerant plant and the other is from a freezing intolerant plant.

22. The method of claim 18, wherein either one of the first tissue and the second tissue is:
   (i) from a drought tolerant plant and the other is from a drought intolerant plant; or
   (ii) from a pathogen resistant plant or pest resistant plant and the other is from a pathogen susceptible plant or pest susceptible plant.

23. The method of claim 18, wherein at least one trait selected from the group consisting of: perenniality, herbicide resistance, pathogen resistance, insect resistance, mite resistance, nematode resistance, parasitic plant resistance, herbivory resistance, nitrogen fixation, heat tolerance, wind tolerance, heavy metal tolerance, flooding and hypoxic stress tolerance, ozone tolerance, higher yield, lodging resistance, greater facilitation of mechanisation, anti-shattering of pods or seeds, altered plant height and stature, increased biomass, lower utilization of fertilizer, faster life-cycle, higher nutritional content, improved baking, milling and malting quality, improved taste, improved colour and longer shelf-life is conferred to the regenerated hybrid monocot tissue or plant.

24. The method of claim 19, wherein the C3 plant is bread wheat (*Triticum aestivum*) and the C4 plant is pearl millet (*Pennisetum glaucum*).

\* \* \* \* \*